United States Patent [19]

Meins et al.

[11] 4,222,904
[45] Sep. 16, 1980

[54] 13-OXABICYCLO[10.3.0]PENTADECANE, ITS PREPARATION AND USE IN PERFUME COMPOSITIONS AND AS AN ODORANT

[75] Inventors: Peter Meins, Mettmann; Klaus Bruns, Krefeld-Traar, both of Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 16,548

[22] Filed: Mar. 1, 1979

[30] Foreign Application Priority Data

Mar. 9, 1978 [DE] Fed. Rep. of Germany ....... 2810107

[51] Int. Cl.² ............................................. C07D 307/93
[52] U.S. Cl. ............................ 252/522 R; 260/346.22
[58] Field of Search ................ 260/346.22; 252/522 R

[56]  References Cited
U.S. PATENT DOCUMENTS 3,085,107  4/1963  Lafont et al. .................. 252/522 R
3,856,815  12/1974  Hopp et al. ...................... 260/345.2

Primary Examiner—Henry R. Jiles
Assistant Examiner—Bernard Dentz
Attorney, Agent, or Firm—Hammond & Littell, Weissenberger and Muserlian

[57]  ABSTRACT

13-Oxabicyclo[10.3.0]pentadecane having the structural formula:

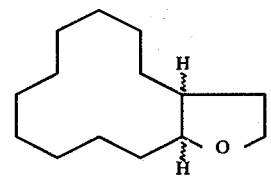

its synthesis, its use as a perfumery agent and as an olefactant component in perfume compositions and as an odorant agent for technical products.

6 Claims, No Drawings

13-OXABICYCLO[10.3.0]PENTADECANE, ITS PREPARATION AND USE IN PERFUME COMPOSITIONS AND AS AN ODORANT

BACKGROUND OF THE INVENTION

The present invention relates to polycyclic oxa-pentadecanes and more particularly to 13-oxabicyclo[10.3.0]pentadecane, its preparation; perfume compositions containing the same; and a method of imparting pleasant odors to objects with such compositions.

OBJECTS OF THE INVENTION

Objects of the present invention are the development of 13-oxabicyclo[10.3.0]pentadecane, a process for its production, and use of the same as a perfumery agent.

These and other objects will become more apparent as the description thereof proceeds.

DESCRIPTION OF THE INVENTION

The novel compound, 13-oxabicyclo[10.3.0]pentadecane having the formula V:

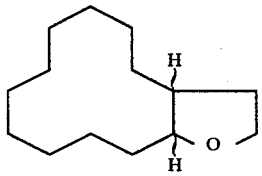

has physical properties and odorant qualities that make it a valuable perfume with a warm amber nuance and good odor persistancy.

The new compound according to the invention is synthesized by the following procedure. Cyclododecanone (I) is condensed with a bromoacetic ester to form the corresponding hydroxyester (II). The hydroxyester is rearranged to the oxabicyclo pentadecane lactone (III) by heating in a strongly acid medium. This lactone is converted with an alkali metal borohydride, such as potassium, sodium or lithium borohydride in isopropanol to the diol (IV), from which 13-oxabicyclo[10.3.0-]pentadecane (V) is obtained by dehydration in toluene in the presence of p-toluene sulfonic acid. The 13-oxabicyclo[10.3.0]pentadecane is formed as a mixture of two stereo isomers in a ratio of about 2:1. The synthesis takes place according to the following reaction scheme:

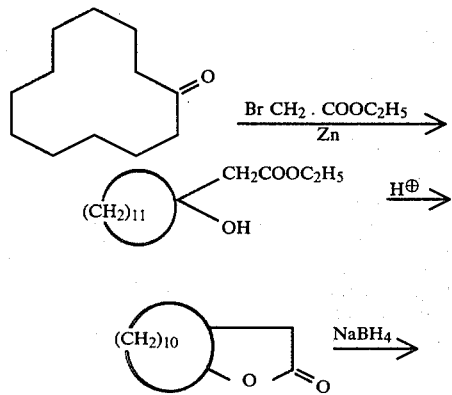

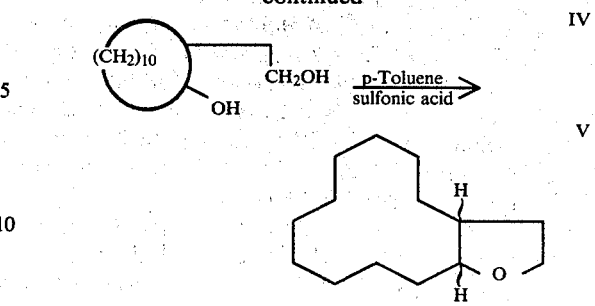

More particularly, the invention involves the process for the preparation of 13-oxabicyclo[10.3.0]pentadecane which comprises the steps of:
(a) condensing cyclododecanone with an ester of bromoacetic acid to form a (1-hydroxy-cyclododecyl)-acetic acid ester;
(b) rearranging said (1-hydroxy-cyclododecyl)-acetic ester to the (2-hydroxy-cyclododecyl)-acetic acid lactone in the presence of a strong acid;
(c) reducing the resulting lactone by reaction with an alkali metal borohydride to form the corresponding 2-(2-hydroxy-cyclododecyl)-ethanol;
(d) dehydrating said 2-(2-hydroxy-cyclododecyl)-ethanol to form 13-oxabicyclo[10.3.0]pentadecane; and
(e) recovering said 13-oxabicyclo[10.3.0]pentadecane in the form of its two stereoisomers or mixtures of said stereoisomers.

13-Oxabicyclo[10.3.0]pentadecane is characterized by a pleasant warm amber nuance, as well as by extremely good odor persistancy. One of the advantages is its excellent ability to combine with other odor notes to form new compositions in which it provides a good background and good persistance.

13-Oxabicyclo[10.3.0]pentadecane can be mixed with other perfumes in various mixing ratios to form new perfume compositions. In general, it is used in perfume compositions in concentrations of between 1% and 50% by weight, related to the entire composition.

Such compositions can be used directly as perfumes or for perfuming cosmetics, such as creams, lotions, toilet water, aerosols, toilet soaps, etc. The composition can also be used to improve or reodor the odor of technical products, such as washing and cleaning agents, soft rinses, textile reagents. For perfuming the various products, the compositions are generally added in effective amounts in concentrations of 0.05 to 5% by weight. From 0.05 to 2% by weight suffices for most perfumery purposes but greater amounts may be needed when used as a reodorant.

The following examples will illustrate the subject of the invention, without limiting it, however, to these examples.

EXAMPLES

Preparation of 13-Oxabicyclo[10.3.0]Pentadecane (a) Preparation of the (1-Hydroxy-Cyclododecyl)-Acetic Acid Ester A solution of cyclododecanone 182 gm (1 mol) and 167 gm (1 mol) of ethyl bromoacetate in toluene/benzene (140/160 ml) was added dropwise over a period of four hours, under stirring and at reflux, to a suspension of 33 gm of zinc powder in toluene/benzene (140/160 ml), which had been activated with a few iodine crystals. After completion of the addition, the mixture was heated for an additional two hours at reflux. The zinc powder used was pre-treated as follows: The zinc powder was stirred for about 20 minutes in 10% aqueous hydrochloric acid, then drained off, washed neutral with water, and washed dry with acetone. Subsequently, it was dried under vacuum at 50° C.

After cooling, the reaction mixture was dissolved with stirring and cooling in about 300 ml of ice cold sulfuric acid (10%). The organic phase was separated and washed with 2 N sodium hydroxide solution, then with 2 N sulfuric acid, and finally was washed neutral with water. After drying over sodium sulfate, the solvent was distilled at reduced pressure and the (1-hydroxy-cyclododecyl)-acetic acid ester obtained was freed from unreacted cyclododecanone under high vacuum by an oil pump vacuum.

(b) Preparation of the Lactone

The above-obtained ester raw product (270 gm) was mixed under strong stirring at 60° C. with 1080 ml of an 80% aqueous sulfuric acid. The mixture was intensively stirred at 60° C. for one hour and then poured on ice to cool. The solution was subsequently stirred until the ice was completely melted and then extracted with ether. The ethereal phase was washed with 2 N sodium hydroxide solution and then washed until neutral with water. After drying over sodium sulfate and distilling off the solvent, the (2-hydroxy-cyclododecyl)-acetic acid lactone was recovered as a crystalline mass.

(c) Preparation of the Diol

The above-obtained raw lactone (204 gm) was dissolved in 3600 ml of isopropanol. 45.6 gm (1.2 mol) of sodium borohydride were added thereto under stirring and the mixture was stirred for three hours while heating to reflux. After the reaction was completed, the mixture was poured into twice its volume of water. The aqueous mixture was extracted several times with ether. The ethereal extracts were combined and dried. The solvent was driven off and the raw product was distilled in the vacuum of an oil pump.

The diol obtained is a colorless, viscous liquid; B.P. 0.6 mm Hg, 172°–175° C.

(d) Preparation of 13-Oxabicyclo[10.3.0]Pentadecane

The diol obtained (208 gm) was dissolved in 640 ml of toluene. Then 17.2 gm of p-toluene sulfonic acid were added and the solution was refluxed for two hours with separation of water. After the reaction was completed, the product was washed with 2 N sodium hydroxide solution, then with water until neutral. The solution was then dried over sodium sulfate. After the solvent was removed, the product was distilled under oil pump vacuum. The 13-oxabicyclo[10.3.0]pentadecane obtained is a colorless liquid with the following characteristics:

B.P. 0.15 mm Hg, 92°–94° C.

IR (film) 1000 to 1100, max. 1057/cm (CH—O—CH$_2$).

1H-NMR δ 3.82 (t, 2H) (O—C$\underline{H}$$_2$).

The odor is characterized as a warm amber nuance.

EXAMPLE 1

Perfume Composition Wood-Amber Base

| | Parts by Weight |
|---|---|
| 13-Oxabicyclo [10.3.0] pentadecane | 250 |
| Boiseambrene (Henkel KGaA) | 250 |
| Cedryl acetate | 250 |
| Cinnamic alcohol | 80 |
| Ionone | 70 |
| Galaxolid (IFF) | 70 |
| Methylnonyl acetaldehyde 5% in DEP | 30 |

EXAMPLE 2

Synthetic Amber Composition

| | Parts by Weight |
|---|---|
| 13-Oxabicyclo [10.3.0] pentadecane | 250 |
| Boiseambrene (Henkel KGaA) | 250 |
| Muskatel sage oil | 140 |
| Methyl ionone | 100 |
| Cedrenol | 50 |
| 2-acetyl-4-isopropyl-5,5-dimethyl-1,3-dioxane | 50 |
| Ketone musk | 50 |
| res. Benzoe Siam | 30 |
| res. Tolu | 30 |
| Pentadecanolide | 20 |
| Patchouli oil | 20 |
| Ethyl vanillin | 10 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:
1. 13-Oxabicyclo[10.3.0]pentadecane.
2. A perfumery composition consisting essentially of from 1% to 50% by weight of the compound 13-oxabicyclo[10.3.0]pentadecane according to claim 1 and the remainder customary constituents of perfumery compositions.
3. The method of imparting a pleasant odor to a product comprising the step of adding to said product a sufficient amount of the perfumery composition according to claim 2 to provide the desired degree of odor.
4. The method according to claim 3 wherein the effective amount consists of 0.05% to 5% by weight of the composition of claim 2.
5. The process for the preparation of 13-oxabicyclo[10.3.0]pentadecane which comprises the steps of:
 (a) condensing cyclododecanone with an ester of bromoacetic acid to form a (1hydroxy-cyclocodecyl)-acetic acid ester;
 (b) rearranging said (1-hydroxy-cyclododecyl)-acetic acid ester to the (2-hydroxy-cyclododecyl)-acetic acid lactone in the presence of a strong acid;
 (c) reducing the resulting lactone by reaction with an alkali metal borohydride to form the corresponding 2-(2-hydroxy-cyclododecyl)-ethanol;
 (d) dehydrating said 2-(2-hydroxy-cyclododecyl)-ethanol to form 13-oxabicyclo[10.3.0]pentadecane; and
 (e) recovering said 13-oxabicyclo[10.3.0]pentadecane in the form of its two stereoisomers or mixtures of said stereoisomers.
6. The process according to claim 5 wherein the ester for condensation step (a) is the ethyl bromoacetate; the alkali metal borohydride is selected from the group consisting of sodium borohydride, potassium borohydride, and lithium borohydride; and the dehydrating step utilizes a toluene sulfonic acid as the dehydrating agent.

* * * * *